(12) United States Patent
Buratynski et al.

(10) Patent No.: US 6,374,661 B1
(45) Date of Patent: *Apr. 23, 2002

(54) REALISTIC, REPEATABLE AND CONTROLLABLE DROP TESTING

(75) Inventors: Edward K. Buratynski, Lawrenceville; Suresh Goyal, Warren; Eugene J. Rosenthal, Edison, all of NJ (US)

(73) Assignee: Lucent Technologies Inc., Murray Hill, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/162,751

(22) Filed: Sep. 29, 1998

(51) Int. Cl.[7] ................................................. G01N 3/30
(52) U.S. Cl. ..................................................... 73/12.06
(58) Field of Search ........................... 73/12.01, 12.04, 73/12.05, 12.06, 12.09, 12.13

(56) References Cited

U.S. PATENT DOCUMENTS 3,209,580 A * 10/1965 Colby ........................ 73/12.06
3,224,249 A * 12/1965 Ford et al. .................. 73/12.06
3,426,578 A * 2/1969 Bergs et al. ................ 73/12.06

* cited by examiner

*Primary Examiner*—Robert Raevis
(74) *Attorney, Agent, or Firm*—Eugene J. Rosenthal

(57) ABSTRACT

Drop testing is performed by controlling the position of a product to be tested with respect to the drop surface until just before the initial impact and then the product is allowed to impact like a free body. Advantageously, realistic, controllable, and substantially repeatable free drop testing can be achieved. In one embodiment of the invention the product is suspended at an angle from a falling structure, e.g., using at least one string or wire, and the suspending material is effectively released just prior to initial impact. By effectively released it is meant actually released, or the effect of the suspending material is essentially negligible, e.g., where the suspending material produces a very low restitutional force when deformed, such as a weak rubber band. The suspension of the object is arranged in such a way that initial impact occurs at the desired point on the product. To this end, depending on the configuration of the object and the number of suspending elements available, it may be necessary that the point of initial impact remain in contact with a platform, which may be part of the structure, that drops along with the product, such as a conventional drop table. In another embodiment of the invention, the drop surface may be moved with respect to the product rather than the product moving with respect to the surface.

32 Claims, 7 Drawing Sheets

REALISTIC, REPEATABLE AND CONTROLLABLE DROP TESTING

TECHNICAL FIELD

This invention relates to the field of drop testing, and more particularly, to the drop testing of products to understand their behavior during a drop and to determine their reliability after being dropped.

BACKGROUND OF THE INVENTION

In the prior art, it is known that a product can be drop tested by simply dropping it from a prescribed height. This is known as free drops. However, the angle and location of impact of the product against the floor cannot be precisely controlled, nor can such impacts be reliably repeated. It is also difficult to outfit the product with measuring instruments to obtain information about forces and deformations that occur during the test. This difficulty arises, at least in part, because the product may land a) at an orientation that is incompatible with the measuring instrument, b) on the measuring instrument itself, thereby destroying it, or c) on the connecting wire of the measuring instrument.

Prior art repeatable and controlled drop testing of a product involves the attaching of the product onto a platform which is then dropped in a controlled and repeatable manner, so that when the platform reaches the end of its travel it subjects the product to a shock pulse, the duration and amplitude of which was previously specified. This is known as drop-table type drop testing. However, because the product is on the platform, the product is subjected to the shock pulse as if the product fell flat on the floor and impacted thereon with the face of the product that is against the platform. Moreover, because the product is attached to the platform, the motion of the product is substantially restricted, and so the product does not move in accordance with its natural dynamic.

SUMMARY OF THE INVENTION

We have recognized that in the real world products do not necessarily fall neatly on a face, as is simulated by the prior art repeatable and controlled drop testing. Instead, products when they fall tend to land in such a way as to clatter, i.e., they rotate and have multiple impacts with the ground during the course of a single drop, and to chatter. Furthermore, we have recognized that the velocities and forces of secondary impacts may be greater than the force of the initial impact with the ground, and that different parts of the product are subject to different accelerations due to rotation of the product after the initial impact. Thus, conventional drop table type drop testing is insufficient to accurately assess the behavior of a product in a real drop.

Therefore, in accordance with the principles of the invention, drop testing is performed by controlling the position of the product with respect to the drop surface until just before the initial impact, and then the product is allowed to impact like a free body. Advantageously, realistic, controllable. and substantially repeatable free drop testing can be achieved.

In one embodiment of the invention the product is suspended at an angle from a falling structure, e.g., using at least one string or wire, and the suspending material is effectively released just prior to initial impact. By effectively released it is meant actually released, or the effect of the suspending material is essentially negligible, e.g., where the suspending material produces a very low restitutional force when deformed, such as a weak rubber band. The suspension of the object is arranged in such a way that initial impact occurs at the desired point on the product. To this end, depending on the configuration of the object and the number of suspending elements available, it may be necessary that the point of initial impact remain in contact with a platform, which may be part of the structure, that drops along with the product, such as a conventional drop table.

In another embodiment of the invention, the drop surface may be moved with respect to the product rather than the product moving with respect to the surface.

DETAILED DESCRIPTION

Figure 1:
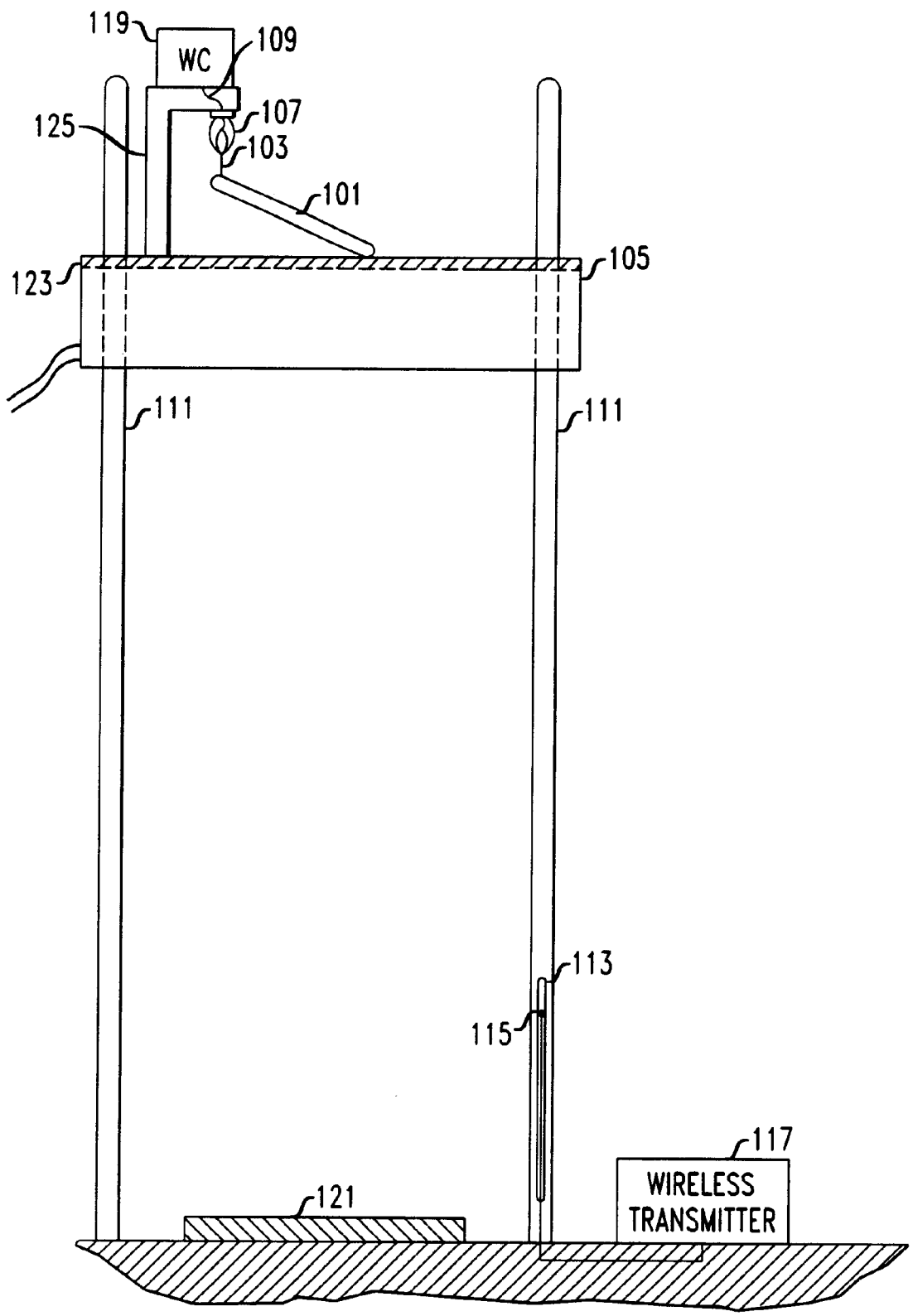
FIG. 1 shows an exemplary drop-table-type embodiment of the invention.

The following merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the block diagrams herein represent conceptual views of illustrative circuitry embodying the principles of the invention. Similarly, it will be appreciated that any flow charts, flow diagrams, state transition diagrams, pseudocode, and the like represent various processes which may be substantially represented in computer readable medium and so executed by a computer or processor, whether or not such computer or processor is explicitly shown.

The functions of the various elements shown in the FIGs., including functional blocks labeled as "processors" may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, read-only memory (ROM) for storing software, random access memory (RAM), and non-volatile storage. Other hardware, conventional and/or custom, may also be included. Similarly, any switches shown in the FIGS. are conceptual only. Their function may be carried out through the operation of program logic, through dedicated logic, through the interaction of program control and dedicated logic, or even manually, the particular technique being selectable by the implementor as more specifically understood from the context.

In the claims hereof any element expressed as a means for performing a specified function is intended to encompass any way of performing that function including, for example, a) a combination of circuit elements which performs that function or b) software in any form, including, therefore, firmware, microcode or the like, combined with appropriate circuitry for executing that software to perform the function. The invention as defined by such claims resides in the fact that the functionalities provided by the various recited means are combined and brought together in the manner which the claims call for. Applicant thus regards any means which can provide those functionalities as equivalent as those shown herein.

An impact between two bodies for purposes of drop testing is said to occur when the bodies are in contact at at least a point with relative velocity toward each other along the normal to the tangent plane at the point of contact.

FIG. 1 shows an exemplary drop-table-type embodiment of the invention. Shown in FIG. 1 are a) product to be drop tested 101, b) suspension 103, c) drop table 105, d) release 107, e) release activator 109, f) guiding rods 111, g) groove 113, h) sensor 115, i) wireless transmitter 117, j) wireless control (WC) 119, k) pulse shaper 121, l) surface material 123, and m) suspension support 125

Product 101 is the product undergoing drop testing. Although the term product is used herein, the use of such term is primarily for the purpose of pedagogical motivation and is not meant as a limitation. Any object desired to be drop tested may be substituted for product 101, and, as such, the more general term object may be used in the claims appended hereto.

Suspension 103 is any mechanism or device that can hold product 101 in a fixed position at an angle relative to the upper surface of drop table 105, i.e., the surface of drop table 105, which may be covered by surface material 123. Items which may be used to implement suspension 103 include one or more strings or wires of any material, one or more various clamps, chain links, ball chain, or the like. Thus, although only a single string is shown in FIG. 1, suspension 103 may be made up of multiple strings, wires, clamps and the like, in any combination required to achieve the desired angle for product 101.

Drop table 105 is a conventional type of drop table. Thus, it is a large heavy block with guide holes passing through it so that the motion of drop table 105 can be constrained by guiding rods 111. The upper surface of drop table 105 may have on it a series of holes so that objects, such as suspension support 125, may be inserted therein and secured to drop table 105. The holes may be arranged in a grid, the spacing of which may be regular or irregular.

Release 107 is any device which is capable of holding and then releasing suspension 103 so that at least product 101 and at least a portion of suspension 103, are free to move independent of any motion of suspension support 125. Release 107 may be electronically activated devices, such as, a jaw, a gripper, a hook, a rocker arm, a magnetic clamp, an unraveling spool, a solenoid, a heatable glue, an explosive mechanism, a blade, a pair scissors, or the like.

Release activator 109 is any control mechanism for activating release 107. For example, it may be a wire or a heater.

Guiding rods 111 guide the motion of drop table 105 to insure that drop table 105 follows a prescribed course, so that the motion of drop table 105 is repeatable. As noted, guiding rods 111 pass through the guide holes of drop table 105. Guiding rods 111 need not be round but can have any arbitrary cross section. Typically some form of friction reduction is used between guiding rods 111 and the guide holes of drop table 105. This friction reduction may be achieved by employing bearings, lubrication, or the like. Such guiding rods and drop tables with holes are well known in the art.

In the exemplary embodiment of the invention shown in FIG. 1, groove 113 is located within one of guiding rods 111. Within groove 113 is located adjustable sensor 115. Sensor 115 may be positioned at various heights within groove 113, as desired by the person conducting the drop tests.

Sensor 115 generates a signal that indicates that drop table 105, or product 101, is passing a specified point in space. Sensor 115 may be any type of sensor, such as a) an optical sensor, b) a mechanical sensor, c) an electrical sensor, d) a magnetic sensor, e) a chemical sensor, or f) the like. Sensor 115 may operate in cooperation with indicators that are on, or within, drop table 105. Although shown in FIG. 1 as being located with groove 113, sensor 115 may be positioned anywhere required to detect that drop table 105 is passing the specified point in space. Thus, the location of sensor 115 is at the discretion of the implementor, subject to the capabilities of sensor 115. Sensor 115 may also be used to measure the velocity, e.g., at impact, of drop table 105.

The signal generated by sensor 115 is communicated, typically, but not necessarily, indirectly to release 107. In the exemplary embodiment of the invention shown in FIG. 1, such communication is achieved by employing wireless transmitter 117, which transmits a wireless signal in response to receiving a signal from sensor 115. Wireless control (WC) 119 receives and detects the wireless signal from transmitter 117, and in response thereto it commands release activator 109 to activate release 107. Although any form of wireless communication may be employed, typically optical or electromagnetic forms are employed. Note that due to the placement of sensor 115 it may be desirable to delay activation of release 107 for a period of time after generation of the signal by sensor 115. Such a delay may be incorporated in, or between, any of the elements along the path from and including sensor 115 to release 107. Although wireless signaling has been employed in the exemplary embodiment of the invention shown in FIG. 1, it is possible to employ wired forms of signaling in addition to such wireless forms, or in lieu thereof.

Pulse shaper 121 may be a conventional pulse shaper which controls the nature of the impact experienced by drop table 105, and ultimately product 101. For effective drop testing, by which is meant product 101 experiences forces in a manner that corresponds to the product being actually dropped, the duration of the pulse generated by the pulse shaper should be much shorter than the shock pulse generated between product 101 and drop table 105. See for example R. E. Newton, *Theory of Shock Isolation* in Shock & Vibration Handbook, Chapter 31, McGraw-Hill, New York, 1988. Additionally, preferably, pulse shaper 121 should provide a dead impact, so that substantially immediately upon impact drop table 105 comes to a complete rest. Otherwise the additional velocity due to the drop table rebound needs to be accounted for, as will be recognized by those skilled in the art.

Surface material 123 is a layer of material that corresponds to the surface against which the drop test is simulating the dropping of the product. For example, surface material 123 may be 1) a layer of hard wood flooring, 2) concrete, 3) carpeting over wood flooring, 4) carpeting over concrete, 5) vegetation covered ground, 6) packed earth, 7) ceramic tile, floor tile, 8) linoleum, 9) blacktop, or 10) any other floor material. Note that in conventional drop tests the effect of the flooring is accounted for by the pulse shaper employed. However, because the pulse shaper is only effective for the initial impact, while a product when it is actually dropped is likely to undergo multiple impacts, and such multiple impacts are likely to be experienced by a product being dropped tested using the exemplary embodiment of the invention shown in FIG. 1, the single pulse shaper is insufficient to provide simulation of the surface. Therefore, instead of providing multiple pulse shapers at each location of impact of product 101, which may be done if desired, it is easier to cover drop table 101 with the actual surface material.

In operation, product 101 is suspended at a desired angle above surface material 123 by suspension 103, with one end or point of product 101 resting on surface material 123. Drop table 105 is then raised to the desired dropping height. The drop height may be specified in any desired manner, e.g., in the conventional manner which is from the bottom of drop table 105 to the top pulse shaper 121. Drop table 105 is then released, e.g., from rest, and permitted to free fall descend as guided by guiding rods 111. In accordance with an aspect of the invention, at a certain height, which is typically set to be a short distance prior to impact, sensor 115 detects the presence of drop table 105 and signals release activator 109, e.g., via wireless transmitter 117 and wireless control (WC) 119, to cause release 107 to release suspension 103. Advantageously, doing so permits product 101 to behave essentially as a free dropping body that is dropping at the same rate as drop table 105 for the rest of the fall.

Upon hitting pulse shaper 121 drop table 105 substantially immediately comes to a halt. This results in an impact between the portion of product 101 which is resting on surface material 123 and surface material 123. The result of this impact will be forces upon product 101 which are substantially the same as those which would have been experienced by product 101 had product 101 been dropped onto surface material 123 and impacted thereon at the desired angle. Because product 101 has been released, it is now free to clatter and chatter in accordance with its natural dynamics and the properties of surface material 123.

Figure 2:
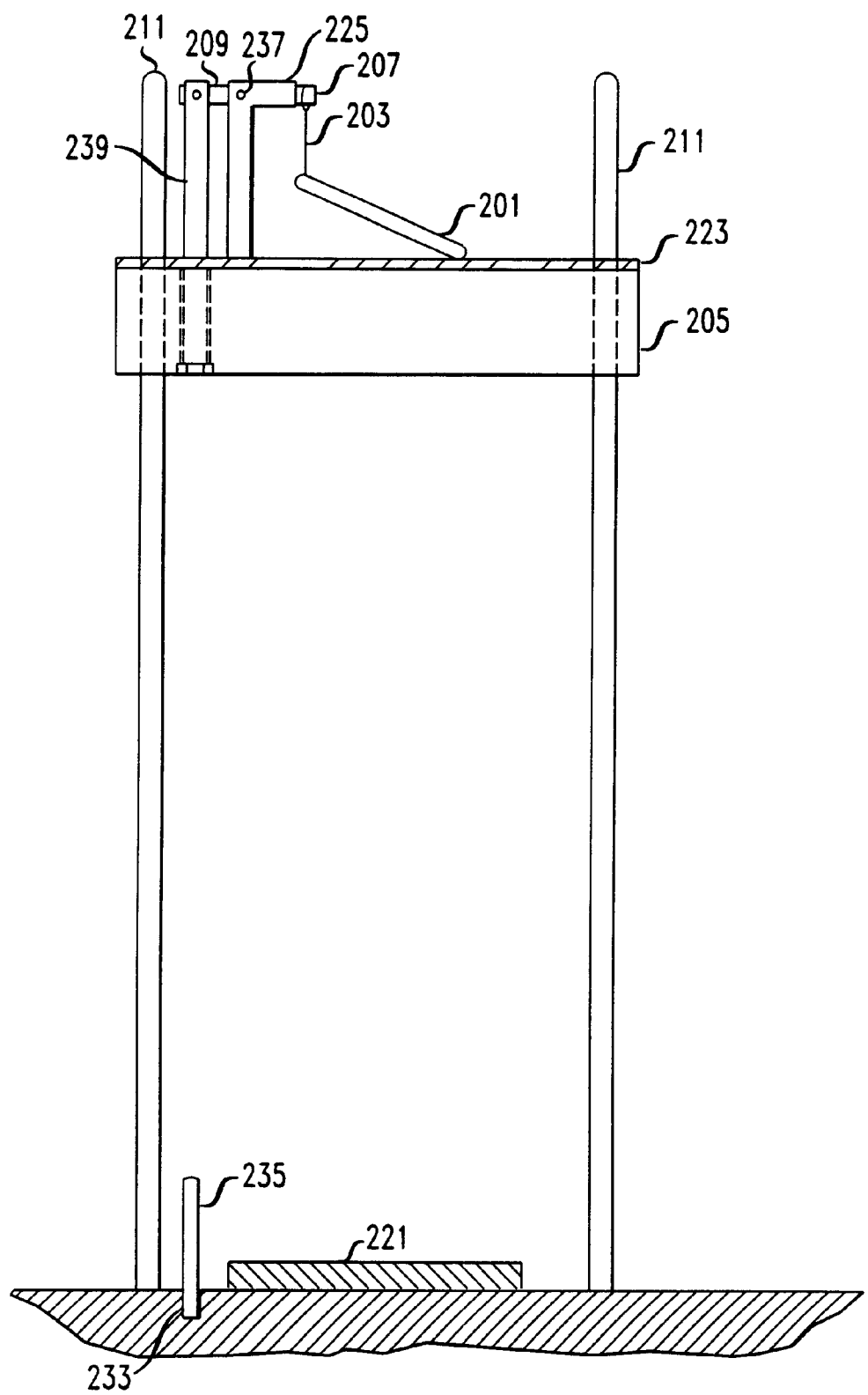
FIG. 2 shows an exemplary mechanical only drop-table-type embodiment of the invention.

FIG. 2 shows an exemplary mechanical only drop-table-type embodiment of the invention. Shown in FIG. 2 are a) product to be drop tested 201, b) suspension 203, c) drop table 205, d) release 207, e) release activator 209, f) guiding rods 211 g) recess 233, h) peg 235, i) pivot 237, j) reciprocating sensor arm 239, k) pulse shaper-221, l) surface material 223, and m) suspension support 225.

Product 201 is the product undergoing drop testing. Drop table 205 is a conventional type of drop table as described above in connection with drop table 105. Pulse shaper 221 may be a conventional pulse shaper and is substantially the same as pulse shaper 121 described in FIG. 1. Surface material 223 is a layer of material that corresponds to the surface against which the drop test is simulating the dropping of the product.

Suspension 203 is any mechanism or device that can hold product 201 in a fixed position at an angle relative to the upper surface of drop table 205. i.e., the surface of drop table 205, which may be covered by surface material 223. Items which may be used to implement suspension 203 include one or more strings or wires of any material. Although only a single string is shown in FIG. 2, suspension 203 may be made up of multiple strings, wires, clamps and the like. in any combination required to achieve the desired angle for product 201. At the end of suspension 203 that is not attached to product 201 there is a loose hook or loop which goes around release 207 and can easily slip off of release 207 when release 207 points downward.

Release 207 is one end of a rocker arm, the other end of which is release activator 209. There may be multiple fingers or teeth to the rocker arm end at which is release 207, each of which may act as to release one or more strings which are part of suspension 203. Release activator 209 is the end of the rocker arm opposite to release 207

Similar to guiding rods 111 of FIG. 1 guiding rods 211 guide the motion of drop table 205 to insure that drop table 205 follows a prescribed course, so that the motion of drop table 205 is repeatable.

Recess 233 is aligned with a hole through drop table 205 into which is fit reciprocating arm 239. The hole is somewhat narrower on the bottom to prevent reciprocating arm 239 from sliding all the way through and out of drop table 205. Into recess 233 is placed a peg, which is narrow enough to fit through the narrow end of the hole in which is resting reciprocating arm 239 and so it can engage reciprocating arm 239 when drop table 205 is low enough. The height of the peg is determinable by the person conducting the drop tests. In an alternative arrangement, a stop can be used to prevent reciprocating arm 239 from falling out of the hole.

In operation, product 201 is suspended at a desired angle above surface material 223 by suspension 203, with one end of product 201 resting on surface material 223. Drop table 205 is then raised to the desired drop height. The drop height may be specified in any desired manner, e.g., in the conventional manner which is from the bottom of drop table 205 to the top pulse shaper 221. Drop table 205 is then released, e.g., from rest, and permitted to free fall descend as guided by guiding rods 211. In accordance with an aspect of the invention, at a certain height, which is determined by the height of peg 235 and how far within drop table 205 reciprocating arm 239 is resting, peg 235 will engage and begin to push upwards reciprocating arm 239. In turn, reciprocating arm 239 will push upward release activator 209, which causes release 207 to begin to move downward, as the rocker arm which is made up of release activator 209 and release 207 rotates around pivot 237. As drop table 205 continues to fall, the upward motion of reciprocating arm 239 and release activator 207 continues, as does the downward movement of release 207. Eventually, the hook on the end of suspension 203 falls off releasing suspension 203. Advantageously, thereafter product 201 may behave essentially as a free dropping body that is dropping at the same rate as drop table 205 for the rest of the fall.

Upon hitting pulse shaper 221 drop table 205 substantially immediately comes to a halt. This results in an impact between the portion of product 201 which is resting on surface material 223 and surface material 223. The result of this impact will be forces upon product 201 which are substantially the same as those which would have been experienced by product 201 had it been dropped onto surface material 223 and impact with the desired angle. Because product 201 has been released, it is now free to clatter and chatter in accordance with its natural dynamics and the properties of surface material 223.

Figure 3:
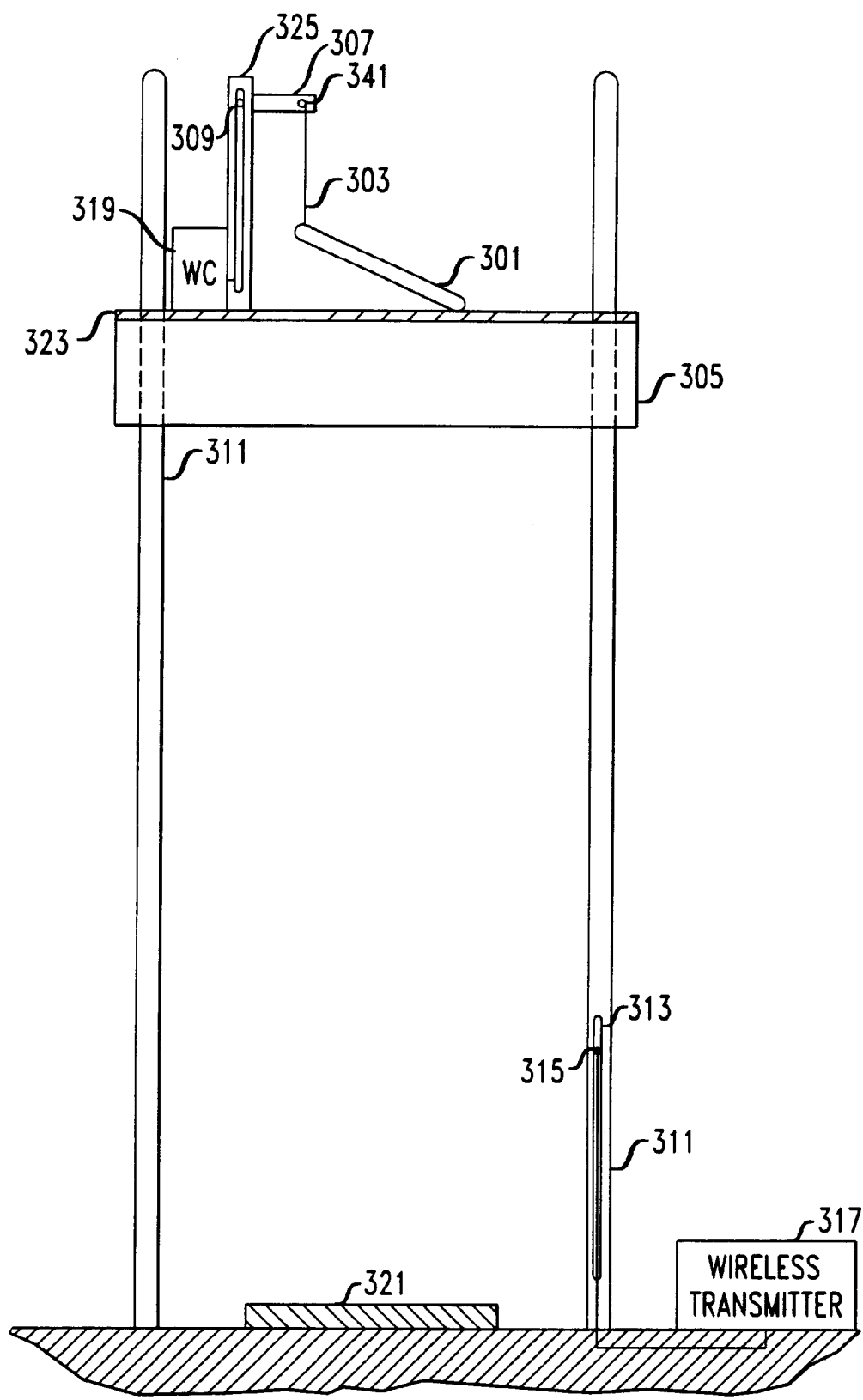
FIG. 3 shows another exemplary drop-table-type embodiment of the invention.

FIG. 3 shows another exemplary drop-table-type embodiment of the invention. Shown in FIG. 3 are a) product to be drop tested 301, b) suspension 303, c) drop table 305, d) release 307, e) release activator 309, f) guiding rods 311, g) groove 313, h) sensor 315, i) wireless transmitter 317, j) wireless control (WC) 319, k) pulse shaper 321, l) surface material 323, and m) suspension support 325

Product 301 is the product undergoing drop testing. Drop table 305 is a conventional type of drop table as described above in connection with drop table 105. Pulse shaper 321 may be a conventional pulse shaper and is substantially the same as pulse shaper 121 described in FIG. 1. Surface material 323 is a layer of material that corresponds to the surface against which the drop test is simulating the dropping of the product.

Suspension 303 is any mechanism or device that can hold product 301 in a fixed position at an angle relative to the upper surface of drop table 305, i.e., the surface of drop table 305, which may be covered by surface material 323. Items which may be used to implement suspension 303 include one or more strings or wires of any material, one or more various clamps, chain links, ball chain, or the like. Thus, although only a single string is shown in FIG. 3, suspension 303 may be made up of multiple strings, wires, and the like, in any combination required to achieve the desired angle for product 301.

Release 307 is a quick release lever which is capable of holding and then releasing suspension 303 so that at least product 301 and at least a portion of suspension 303, are free to move independent of any motion of suspension support 325. Release 307 operates by sliding down within slot 309 at a faster rate than drop table 305 is falling. This may be achieved by a motorized drive within slot 309 which is activated in response to a command initiated by sensor 315, so that slot 309 functions as a release activator. By falling faster than drop table 305 suspension 303 becomes slack, allowing product 301 to behave as if it were naturally dropped. Moreover, advantageously, release 307 can be raised automatically. Doing so retensions suspension 303 and prepares product 301 for another test. Thus, product 301 may be repeatably and automatically tested multiple times.

Release 307 may include, in addition to or in lieu of motorized slot 309, automatically unravelable spool 341. To release, or further release. product 301 to move naturally, spool 341 may be made so that it automatically unravels in response to a command initiated by sensor 315. Such unraveling releases to the tension on suspension 303. Advantageously, spool 341 may automatically rewind around itself suspension 303, so that product 301 may be repositioned for another drop test. Thus, product 301 may be repeatably and automatically tested multiple times.

Note that just as multiple wires may be used for suspending product 301, multiple releases 307 may be used so that product 301 may be released to achieve the desired drop test. Thus, there may be more than one motorized slots, spools, or combinations thereof employed for any particular drop test.

Similar to guiding rods 111 of FIG. 1, guiding rods 311 guide the motion of drop table 305 to insure that drop table 305 follows a prescribed course, so that the motion of drop table 305 is repeatable. In the exemplary embodiment of the invention shown in FIG. 3, groove 313 is located within one of guiding rods 311. Within groove 313 is located adjustable sensor 315. Sensor 315 may be positioned at various heights within groove 313, as desired by the person conducting the drop tests.

Sensor 315 operates in the same manner as sensor 115 of FIG. 1 to generate a signal that indicates that drop table 305, or product 301, is passing a specified point in space. As with sensor 115, sensor 315 need not be located within groove 313. The signal generated by sensor 315 is communicated, typically, but not necessarily, indirectly to release 307, in a manner similar to that described in FIG. 1, e.g., by employing wireless transmitter 317, which transmits a wireless signal in response to receiving a signal from sensor 315. Wireless control (WC) 319 receives and detects the wireless signal from transmitter 317, and in response thereto it commands release activator 309 to activate release 307. As noted above, it may be desirable to delay activation of release 307 for a period of time after generation of the signal by sensor 315.

Drop table 305 is a conventional type of drop table as described above in connection with drop table 105. Pulse shaper 321 may be a conventional pulse shaper and is substantially the same as pulse shaper 121 described in FIG. 1. Surface material 323 is a layer of material that corresponds to the surface against which the drop test is simulating the dropping of the product.

In operation, product 301 is suspended at a desired angle above surface material 323 by suspension 303, with one end of product 301 resting on surface material 323. Drop table 305 is then raised to the desired drop height. The drop height may be specified in any desired manner, e.g., in the conventional manner which is from the bottom of drop table 305 to the top pulse shaper 321. Drop table 305 is then released, e.g., from rest, and permitted to free fall descend as guided by guiding rods 311. In accordance with an aspect of the invention, at a certain height. which is typically set to be a short distance prior to impact, sensor 315 detects the presence of drop table 305 and signals release activator 309, e.g., via wireless transmitter 317 and wireless control (WC) 319, to cause release 307 to release suspension 303. This is achieved by having release 307 slide down within slot 309 at a faster rate than drop table 305 is falling and/or having automatically unravelable spool 341 unravel. Advantageously, doing so permits product 301 to behave essentially as a free dropping body that is dropping at the same rate as drop table 305 for the rest of the fall.

Upon hitting pulse shaper 321 drop table 305 substantially immediately comes to a halt. This results in an impact between the portion of product 301 which is resting on surface material 323 and surface material 323. The result of this impact will be forces upon product 301 which are substantially the same as those which would have been experienced by product 301 had it been dropped onto surface material 323 and impacted thereon at the desired angle. Because product 301 has been released, it is now free to clatter and chatter in accordance with its natural dynamics and the properties of surface material 323.

After a time, product 301 will come to a rest on drop table 305. At such a time, e.g., which may be specified by a timer circuit, release 307 may then be automatically raised within slot 309 and/or unravelable spool 341 may be rewound so as to take up slack in suspension 303. Also, drop table 305 may be automatically raised to a height from which a next drop test is to be performed. Thus, advantageously, the entire system is reset to perform another drop test on product 301.

Figure 4:
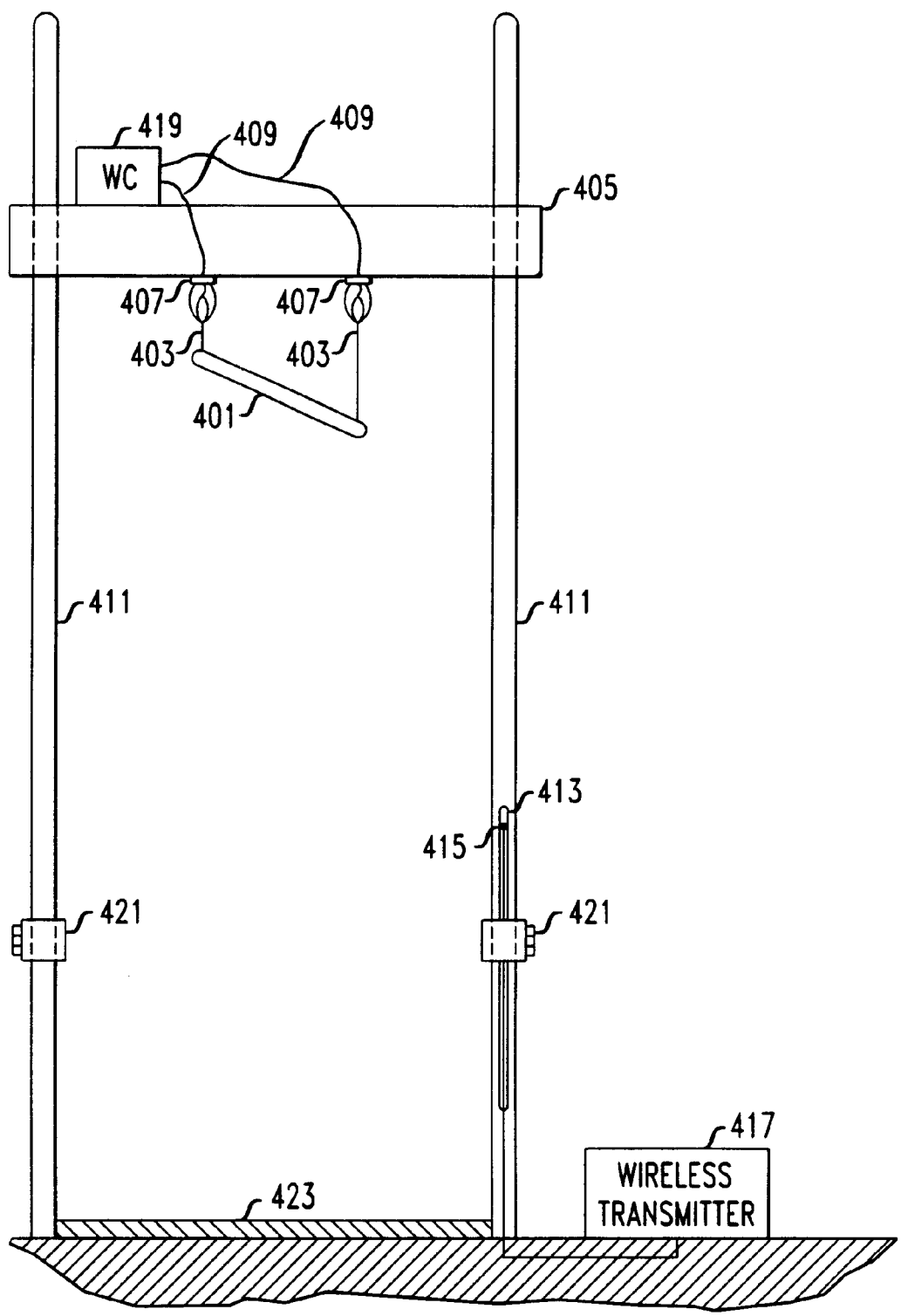
FIG. 4 shows an exemplary suspension-type embodiment of the invention.

FIG. 4 shows an exemplary suspension-type embodiment of the invention. Shown in FIG. 4 are a) product to be drop tested 401 b) suspension 403, c) suspension platform 405, d) release 407, e) release activators 409, f) guiding rods 411, g) groove 413, h) sensor 415, i) wireless transmitter 417, j) wireless control (WC) 419, k) adjustable stops 421, and l) surface material 423.

Product 401 is the product undergoing drop testing. Suspension 403 is any mechanism or device that can hold product 401 in a fixed position at an angle relative to the lower surface of suspension platform 405, i.e., at an angle fixed with respect to surface material 423. Items which may be used to implement suspension 403 include one or more strings or wires of any material, one or more various clamps, chain links, ball chain, or the like. Thus, although only two strings are shown in FIG. 4, suspension 403 may be made up of additional strings, wires, clamps and the like, in any combination required to achieve the desired angle for product 401. Suspension 403 may also be made of rigid materials, e.g., electromagnetic rods.

Suspension platform 405 is a platform, such as a block, with guide holes passing through it so that the motion of suspension platform 405 can be constrained by guiding rods 411. The lower surface of suspension platform 405 may have on it a series of holes so that various ones of releases 407 may be contained therein and secured thereby to suspension platform 405. The holes may be arranged in a grid, the spacing of which may be regular or irregular.

Release 407 is any device which is capable of holding and then releasing suspension 403 so that at least product 401, and possibly a portion of suspension 403, are free to move independent of any motion of suspension platform 405. Release 407 may be electronically activated devices, such as, a jaw, a gripper, a hook, a rocker arm, a magnetic clamp, an unraveling spool, a solenoid, a heatable glue, an explosive mechanism, a blade, a pair scissors, or the like.

Release activator 409 is any control mechanism for activating release 407. For example, it may be a wire or a heater.

As noted, guiding rods 411 guide the motion of suspension platform 405 to insure that suspension platform 405 follows a prescribed course, so that the motion of suspension platform 405 is repeatable. Guiding rods 411 pass through the guide holes of suspension platform 405. Guiding rods 411 need not be round but can have any arbitrary cross section. Typically some form of friction reduction is used between guiding rods 411 and the guide holes of suspension platform 405. This friction reduction may be achieved by employing bearings, lubrication, or the like. Such guiding rods and suspension platforms with holes are well known in the art.

In the exemplary embodiment of the invention shown in FIG. 4, groove 413 is located within one of guiding rods 411. Within groove 413 is located adjustable sensor 415. Sensor 415 may be positioned at various heights within groove 413, as desired by the person conducting the drop tests.

Sensor 415 generates a signal that indicates that suspension platform 405, or product 401, is passing a specified point in space. Sensor 415 may be any type of sensor, such as a) an optical sensor, b) a mechanical sensor, c) an electrical sensor, d) a magnetic sensor, e) a chemical sensor, or f) the like. Sensor 415 may operate in cooperation with indicators that are on, or within, suspension platform 405.

Although shown in FIG. 4 as being located with groove 413, sensor 415 may be positioned anywhere required to detect that suspension platform 405 is passing the specified point in space. Thus, the location of sensor 415 is at the discretion of the implementor, subject to the capabilities of sensor 415.

The signal generated by sensor 415 is communicated, typically, but not necessarily, indirectly to release 407. In the exemplary embodiment of the invention shown in FIG. 4 such communication is achieved by employing wireless transmitter 417, which transmits a wireless signal in response to receiving a signal from sensor 415. Wireless control (WC) 419 receives and detects the wireless signal from transmitter 417, and in response thereto it commands release activator 409 to activate release 407. Although any form of wireless communication may be employed, typically optical or electromagnetic forms are employed. Note that due to the placement of sensor 415 it may be desirable to delay activation of release 407 for a period of time after generation of the signal by sensor 415. Such a delay may be incorporated in, or between, any of the elements along the path from and including sensor 415 to release 407. Although wireless signaling has been employed in the exemplary embodiment of the invention shown in FIG. 4, it is possible to employ wired forms of signaling in addition to such wireless forms, or in lieu thereof.

Adjustable stops 421 are employed to arrest the motion of suspension platform 405 after release 403 has been activated to release product 401, thereby preventing suspension platform 405 from hitting surface material 423, or from even entering the space within which product 401 is likely to move in after its impact with surface material 423. Additionally, preferably, adjustable stops 421 should provide a dead impact, so that substantially immediately upon impact suspension platform 405 comes to a complete rest.

Surface material 423 is a layer of material that corresponds to the surface against which the drop test is simulating the dropping of the product such as described hereinabove.

In operation, product 401 is suspended above surface material 423 by suspension 403 and is positioned at an angle that it is desired that product 401 will have upon initial impact with surface material 423. Suspension platform 405 is then raised to the desired drop height. The drop height may be specified in any desired manner, such as the distance from the lowest point of suspend product 401 to surface material 423. Suspension platform 405 is then released, e.g., from rest, and permitted to free fall descend as guided by guiding rods 411. In accordance with an aspect of the invention, at a certain height sensor 415 detects the presence of suspension platform 405, or possibly even the presence of product 401, and signals release activator 409, e.g., via wireless transmitter 417 and wireless control (WC) 419, to cause release 407 to release suspension 403. Advantageously, doing so permits product 401 to become a free dropping body for the rest of the fall. Note that initially product 401 is dropping at the same rate as suspension platform 405, and that because of the laws of mechanics product 401 will continue to fall and to maintain the angle at which is was suspended for the drop test.

Upon hitting adjustable stops 421 suspension platform 405 substantially immediately comes to a halt. However, product 401 continues to fall in accordance with the principles of mechanics, and so, in accordance with an aspect of the invention, product 401 maintains its relative angle with respect to surface material 423. Eventually product 401 impacts on surface material 423. The result of this impact will be forces upon product 401 which are substantially the same as those which would have been experienced by product 401 had it been dropped onto surface material 423 and impacted thereon at the desired angle. Furthermore, because product 401 has been released, it is now free to clatter and chatter in accordance with its natural dynamics and the properties of surface material 423.

Figure 5:
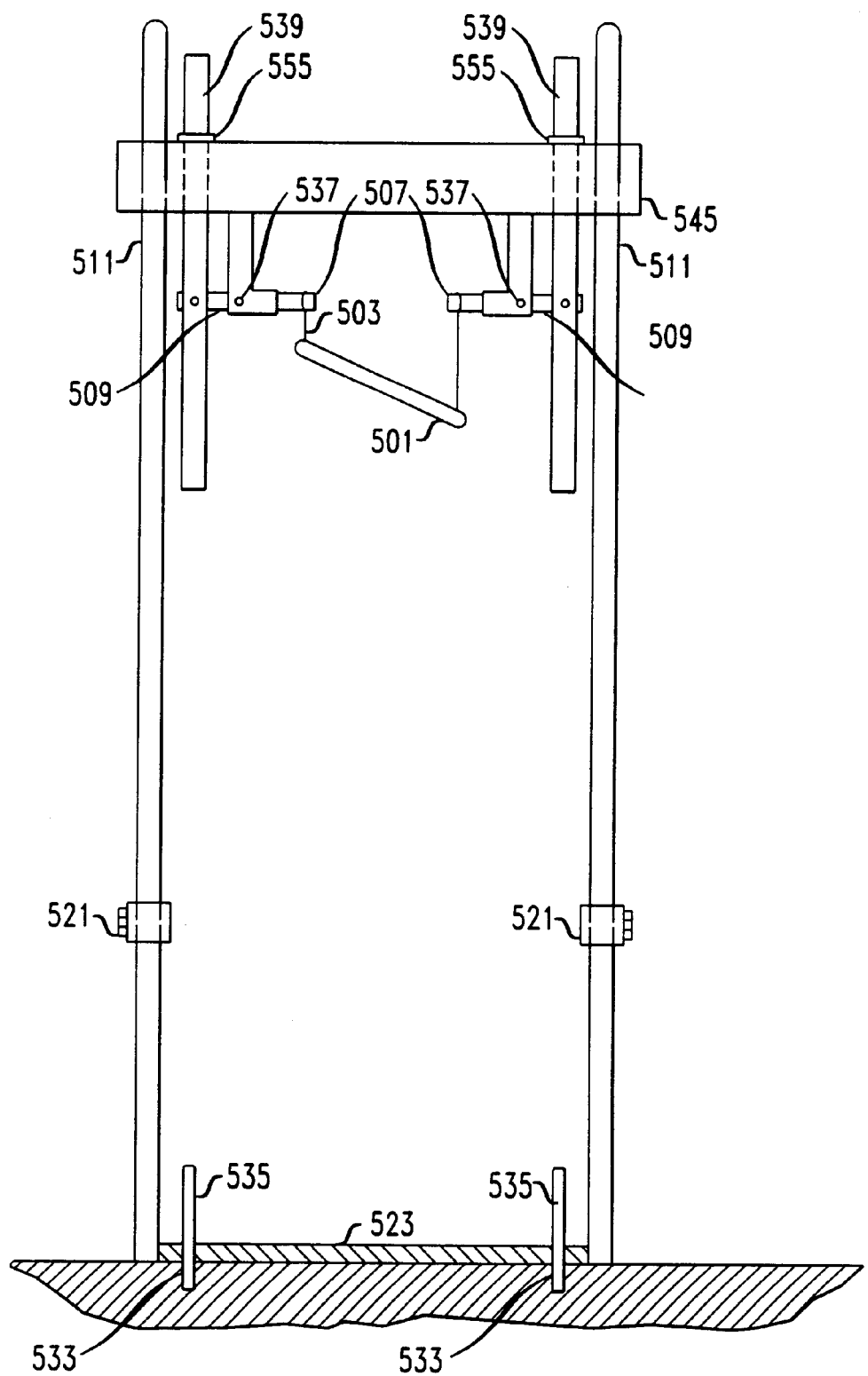
FIG. 5 shows an exemplary mechanical only suspension-type embodiment of the invention.

FIG. 5 shows an exemplary mechanical only suspension-type embodiment of the invention. Shown in FIG. 5 are a) product to be drop tested 501, b) suspension 503, c) suspension platform 505, d) release 507, e) release activator 509, f) guiding rods 511, g) recesses 533, h) pegs 535, i) pivots 537, j) reciprocating sensor arms 539, k) adjustable stops 521, and l) surface material 523.

Product 501 is the product undergoing drop testing. Suspension platform 505 is a platform, such as a suspension platform 405 described more thoroughly in connection with FIG. 4. Similar to guiding rods 111 of FIG. 1 , guiding rods 511 guide the motion of suspension platform 505 to insure that suspension platform 505 follows a prescribed course, so that the motion of suspension platform 505 is repeatable.

Suspension 503 is any mechanism or device that can hold product 501 in a fixed position at an angle relative to the lower surface of suspension platform 505, i.e., at an angle fixed with respect to surface material 523. Items which may be used to implement suspension 503 include one or more strings or wires of any material, one or more various clamps, chain links, ball chain, or the like. Thus, although only two strings are shown in FIG. 5, suspension 503 may be made up of additional strings, wires. clamps and the like, in any combination required to achieve the desired angle for product 501. At the end of each suspender of suspension 503 that is not attached to product 501 there is a loose hook or loop which goes around a portion of release 507 and can easily slip off of that portion of release 507 when it is pointed downward.

Each portion of release 507 is one end of a rocker arm, the other end of the rocker arm being a portion of release activator 509. There may be multiple fingers or teeth to each rocker arm end that is part of release 507, and each tooth or finger may act to release one or more strings which are part of suspension 503.

Each of recesses 533 is aligned with a corresponding one of reciprocating arms 539. Each of reciprocating arms 539 passes through a hole in suspension platform 505. Reciprocating arms 539 are arranged so that they do not fall out the bottom of their respective holes. This may be achieved by employing a stop, such as stops 555, which is through, or around, each of reciprocating arms 539. Another arrangement contours reciprocating arms 539 with respect to the holes in which they are placed, e.g., the holes and reciprocating arms 539 are somewhat narrower near the bottom of suspension platform 505.

Into each of recesses 533 is placed one of pegs 535, and each peg can engage reciprocating arm 539 when suspension platform 505 is low enough. The height of the peg is determinable by the person conducting the drop tests. Also note that the extension of reciprocating arms 539 below suspension platform 505 need not be uniform. Furthermore, if reciprocating arms 539 are long enough, recesses 533 and pegs 535 may be dispensed with.

Adjustable stops 521 are employed to arrest the motion of suspension platform 505 after release 503 has been activated to release product 501 and to prevent suspension platform 505 from hitting surface material 523, or from even entering the space within which product 501 is likely to move in after its impact with surface material 523. Additionally, preferably, adjustable stops 521 should provide a dead impact, so that substantially immediately upon impact suspension platform 505 comes to a complete rest.

Surface material 523 is a layer of material that corresponds to the surface against which the drop test is simulating the dropping of the product such as described hereinabove.

In operation, product 501 is suspended at a desired angle above surface material 523 by suspension 503. Suspension platform 505 is then raised to the desired drop height. The drop height may be specified in any desired manner, such as the distance from the lowest point of suspend product 501 to surface material 523. Suspension platform 505 is then released, e.g., from rest, and permitted to free fall descend as guided by guiding rods 511.

In accordance with an aspect of the invention, at a certain height, which is determined by the height of pegs 535 and how far each of reciprocating arms 539 extends below the bottom of suspension platform 505, pegs 535 will engage and begin to push upwards reciprocating arms 539. In turn, reciprocating arms 539 will push upward each portion of release activator 509, which causes each portion of release 507 to begin to move downward, as each rocker arm which is made up of a portion of release activator 509 and a portion of release 507 rotates around its respective pivot 537. As suspension platform 505 continues to fall, the upward motion of each reciprocating arm 539 and each portion of release activator 507 continues, as does the downward movement of each portion of release 507. Eventually, each hook on the end of each portion of suspension 503 falls off, releasing suspension 503. Advantageously, thereafter product 501 may behave essentially as a free dropping body that is dropping at the same rate as suspension platform 505 for the rest of the fall. Note that initially product 501 is dropping at the same rate as suspension platform 505, and that because of the laws of mechanics product 501 will continue to fall and to maintain the angle at which is was suspended for the drop test.

Upon hitting adjustable stops 521 suspension platform 505 substantially immediately comes to a halt. However, product 501 continues to fall. Eventually product 501 impacts on surface material 523. The result of this impact will be forces upon product 501 which are substantially the same as those which would have been experienced by product 501 had it been dropped onto surface material 523 and impacted thereon at the desired angle. Furthermore, because product 501 has been released, it is now free to clatter and chatter in accordance with its natural dynamics and the properties of surface material 523.

In an alternative embodiment of the invention, suspension 503 could pass through holes in suspension platform 505, and release 507 and release activator 509 could be located on top of suspension platform 505, and be arranged in a manner similar to that shown in FIG. 2.

Figure 6:
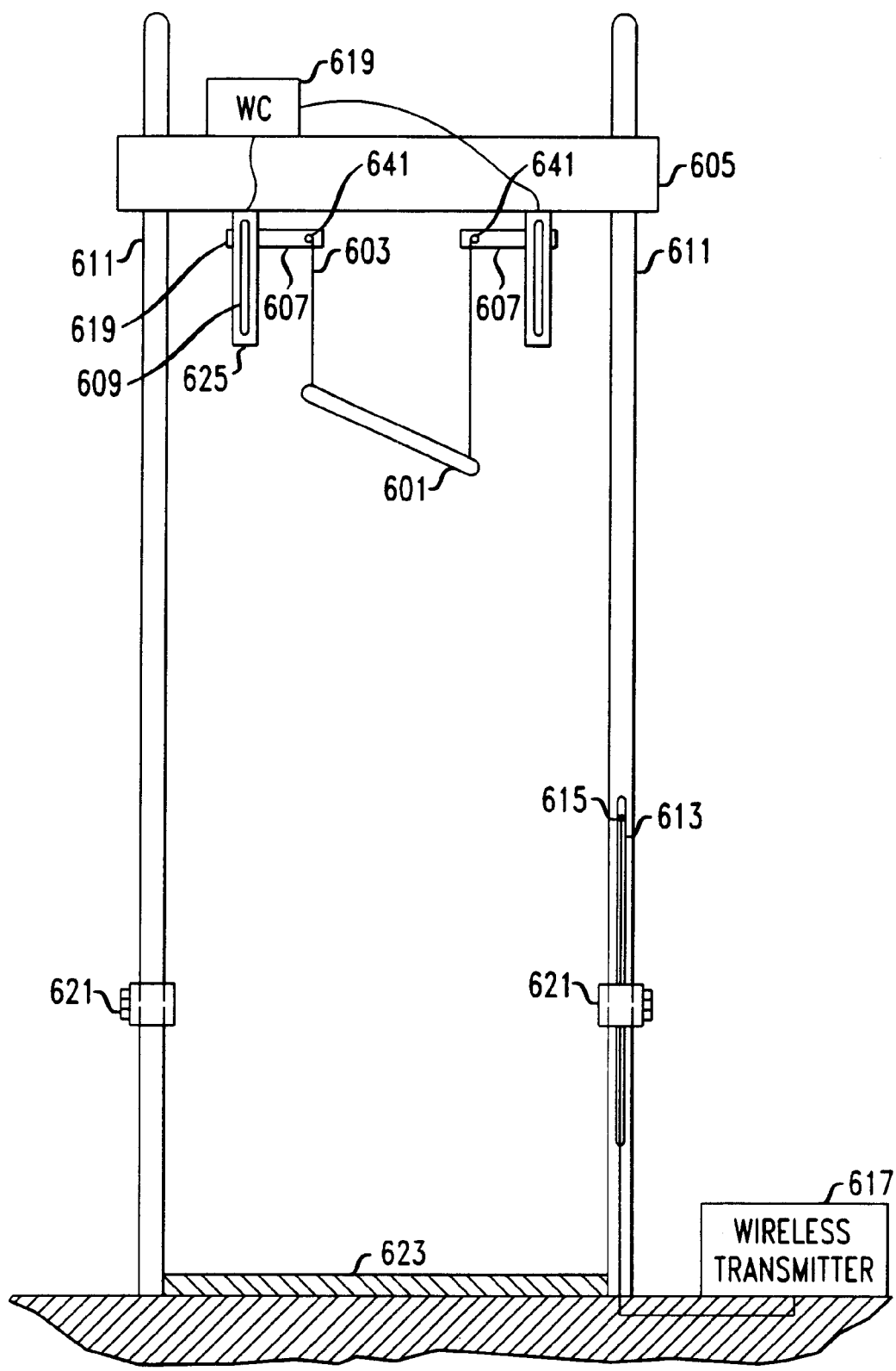
FIG. 6 shows another exemplary suspension-type embodiment of the invention.

FIG. 6 shows another exemplary suspension-type embodiment of the invention. Shown in FIG. 6 are a) product to be drop tested, 601, b) suspension 603, c) suspension platform 605, d) release 607, e) release activator 609, f) guiding rods 611, g) groove 613, h) sensor 615, i) wireless transmitter 617, j) wireless control (WC) 619, k) adjustable stops 621, l) surface material 623, and m) suspension support 625

Product 601 is the product undergoing drop testing. Suspension platform 605 is a platform, such as a suspension platform 405 described more thoroughly in connection with FIG. 4. Similar to guiding rods 111 of FIG. 1, guiding rods 611 guide the motion of suspension platform 605 to insure that suspension platform 605 follows a prescribed course, so that the motion of suspension platform 605 is repeatable. Surface material 623 is a layer of material that corresponds to the surface against which the drop test is simulating the dropping of the product such as described hereinabove.

Suspension 603 is any mechanism or device that can hold product 601 in a fixed position at an angle relative to the lower surface of suspension platform 605, i.e., at an angle fixed with respect to surface material 623. Items which may be used to implement suspension 603 include one or more strings or wires of any material. one or more various clamps, chain links, ball chain, or the like. Thus, although only a single string is shown in FIG. 6, suspension 603 may be made up of multiple strings, wires, and the like, in any combination required to achieve the desired angle for product 601.

Each portion of release 607 may be a quick release lever which is capable of holding and then releasing a portion of suspension 603 so that at least product 601 and at least a portion of suspension 603, are free to move independent of any motion of suspension support 625. Each portion of release 607 operates by sliding down within slot 609 at a faster rate than suspension platform 605 is falling. This may be achieved by a motorized drive within each slot 609 each of which is activated in response to a command initiated by sensor 615, so that each slot 609 functions as a release activator. By falling faster than suspension platform 605 suspension 603 becomes slack, allowing product 601 to behave as if it were naturally dropped. Moreover, advantageously, release 607 can be raised automatically. Doing so retensions suspension 603 and prepares product 601 for another test. Thus, product 601 may be repeatably and automatically tested multiple times.

Any portion of release 607 may include, in addition to or in lieu of motorized slot 609, automatically unravelable spool 641. To release, or further release, product 601 to move naturally, spool 641 may be made so that it automatically unravels in response to a command initiated by sensor 615. Such unraveling releases the tension on suspension 603. Advantageously, spool 601 may automatically rewind around itself suspension 603, so that product 601 may be repositioned for another drop test. Thus, product 601 may be repeatably and automatically tested multiple times.

Note that just as more than two wires may be used for suspending product 601, release 607 may include more than two portions, so that product 601 may be positioned and then released to achieve the desired drop test. Further note that although the apparatus for suspending and releasing product 601 is shown below suspension platform 505, such apparatus could be located above suspension platform 505 with suspension 503 passing through appropriate holes in suspension platform 505.

In the exemplary embodiment shown in FIG. 6, groove 613 is located within one of guiding rods 611. Within groove 613 is located adjustable sensor 615. Sensor 615 may be positioned at various heights within groove 613, as desired by the person conducting the drop tests. Sensor 615 operates in the same manner as sensor 115 of FIG. 1 to generate a signal that indicates that suspension platform 605, or product 601, is passing a specified point in space. The signal generated by sensor 615 is communicated, typically, but not necessarily, indirectly to release 607, in a manner similar to that described in FIG. 1, e.g., by employing wireless transmitter 617, which transmits a wireless signal in response to receiving a signal from sensor 615. Wireless control (WC) 619 receives and detects the wireless signal from transmitter 617. and in response thereto it commands release activator 609 to activate release 607. As noted above, it may be desirable to delay activation of release 607 for a period of time after generation of the signal by sensor 615.

In operation, product 601 is suspended at a desired angle above surface material 623 by suspension 603. Suspension platform 605 is then raised to the desired drop height. The drop height may be specified in any desired manner, such as the distance from the lowest point of suspend product 601 to surface material 623. Suspension platform 605 is then released, e.g., from rest, and permitted to free fall descend as guided by guiding rods 611. In accordance with an aspect of the invention, at a certain height, which is typically set to be a short distance prior to impact, sensor 615 detects the presence of suspension platform 605, or possibly even the presence of product 601, and signals release activator 609, e.g., via wireless transmitter 617 and wireless control (WC) 619, to cause release 607 to release suspension 603. This is achieved by having each portion of release 607 slide down within slot 609 at a faster rate than suspension platform 605 is falling and/or having each automatically unravelable spool 641 unravel. Advantageously, doing so permits product 601 to become a free dropping body for the rest of the fall. Note that initially product 601 is dropping at the same rate as suspension platform 605, and that because of the laws of mechanics product 601 will continue to fall and to maintain the angle at which is was suspended for the drop test.

Upon hitting adjustable stops 621 suspension platform 605 substantially immediately comes to a halt. However, product 601 continues to fall. Eventually product 601 impacts on surface material 623. The result of this impact will be forces upon product 601 which are substantially the same as those which would have been experienced by product 601 had it been dropped onto surface material 623 and impacted thereon at the desired angle. Furthermore, because product 601 has been released, it is now free to clatter and chatter in accordance with its natural dynamics and the properties of surface material 623.

After a time, product 601 will come to a rest on suspension platform 605. At such a time, e.g., which may be specified by a timer circuit, each portion of release 607 may then be automatically raised within its respective slot 609 and/or each unravelable spool 641 may be raveled so as to take up slack in suspension 603. Also, suspension platform 605 may be automatically raised to a height from which a next drop test is to be performed. Thus, advantageously, the entire system is reset to perform another drop test on product 601.

In the embodiments of the invention shown in FIGs. 1–6 it is possible to achieve the effect of a drop of greater height than that to which the product being tested is actually raised. This is achieved by, for an initial period. using non-gravitational power to accelerate the drop table or suspension platform for a period of time. In order that the product being tested also appropriately accelerates in tandem with the drop table or suspension platform, the suspension includes a rigid member which is released prior to impact in accordance with the principles of the invention, possibly even prior to the rest of the suspension, e.g., at the end of the powered acceleration period.

Figure 7:
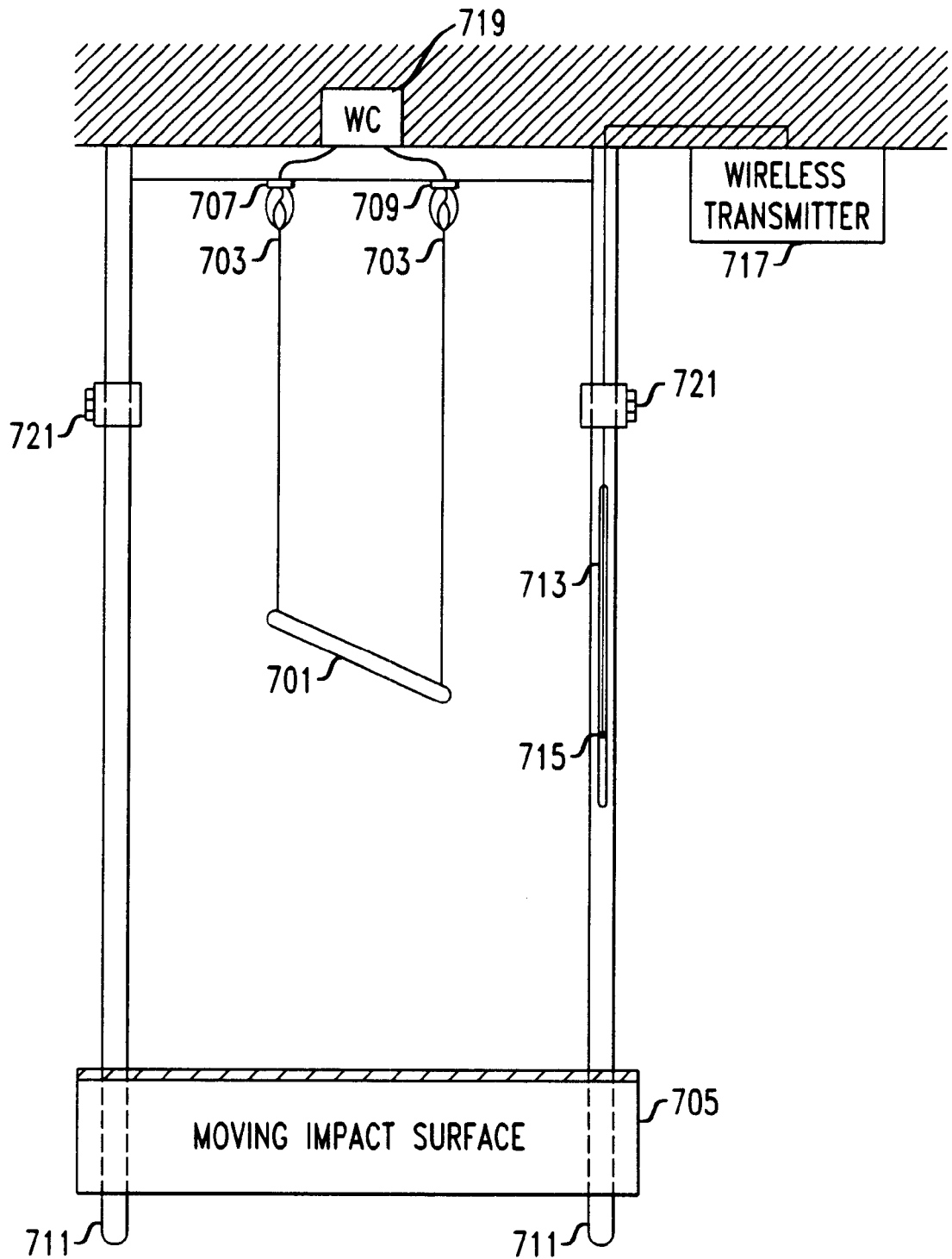
FIG. 7 shows an embodiment of the invention using a moving impact surface.

FIG. 7 shows an embodiment of the invention using a moving impact surface. Note that the arrangement of FIG. 7 actually implements the drop test in reverse, i.e., all momentum prior to impact is within a moving block having thereon the surface against which the test is being conducted rather than the momentum being within the product being tested. Shown in FIG. 7 are a) product to be drop tested 701, b) suspension 703, c) moving block 705, d) releases 707, e) release activators 709, f) guiding rods 711, g) groove 713, h) sensor 715, i) wireless transmitter 717, j) wireless control (WC) 719, k) adjustable stops 721, and l) surface material 723.

Product 701 is the product undergoing drop testing. Suspension 703 is any mechanism or device that can hold product 701 in a fixed position at an angle relative to the upper surface of moving block 705. Items which may be used to implement suspension 703 include one or more strings or wires of any material, one or more various clamps, chain links, ball chain, or the like. Thus, although only two strings are shown in FIG. 7, suspension 703 may be made up of additional strings, wires, clamps and the like, in any combination required to achieve the desired angle for product 701. In this embodiment of the invention it is not recommended that suspension 703 be made of rigid materials.

Moving block 705 is a block, with guide holes passing through it so that the motion of moving block 705 can be constrained by guiding rods 711. Moving block 705 needs to be sufficiently massive with respect to product 701 that an impact by moving block 705 with stationary product 701 has essentially no effect on the velocity of moving block 705.

Release 707 is any device which is capable of holding and then releasing suspension 703 so that at least product 701 is free to move independent of any motion of moving block 705. Release 707 may be electronically activated devices, such as, a jaw, a gripper, a hook, a rocker arm, a magnetic clamp, an unraveling spool, a solenoid, a heatable glue, an explosive mechanism, a blade, a pair scissors, or the like.

Release activator 709 is any control mechanism for activating release 707. For example, it may be a wire or a heater.

Guiding rods 711 guide the motion of moving block 705 to insure that moving block 705 follows a prescribed course, so that the motion of moving block 705 is repeatable. Guiding rods 711 pass through the guide holes of moving block 705. Guiding rods 711 need not be round but can have any arbitrary cross section. Typically some form of friction reduction is used between guiding rods 711 and the guide holes of moving block 705. This friction reduction may be achieved by employing bearings, lubrication, or the like. Such guiding rods and moving blocks with holes are well known in the art.

In the exemplary embodiment shown in FIG. 7, groove 713 is located within one of guiding rods 711. Within groove 713 is located adjustable sensor 715. Sensor 715 may be positioned at various heights within groove 713, as desired by the person conducting the drop tests.

Sensor 715 generates a signal that indicates that moving block 705 is passing a specified point in space. In the embodiment of the invention shown in FIG. 7, preferably, the signal should be generated when the top of moving block 705. which is covered with surface material 723, just reaches the lowest point of product 701 as it is suspended. Sensor 715 may be any type of sensor, such as a) an optical sensor, b) a mechanical sensor, c) an electrical sensor, d) a magnetic sensor, e) a chemical sensor, or f) the like. Sensor 715 may operate in cooperation with indicators that are on, or within, moving block 705. Although shown in FIG. 7 as being located with groove 713, sensor 715 may be positioned anywhere required to detect that moving block 705 is passing the specified point in space. Thus, the location of sensor 715 is at the discretion of the implementor, subject to the capabilities of sensor 715.

The signal generated by sensor 715 is communicated, typically, but not necessarily, indirectly to release 707. In the exemplary embodiment of the invention shown in FIG. 7 such communication is achieved by employing wireless transmitter 717, which transmits a wireless signal in response to receiving a signal from sensor 715. Wireless control (WC) 719 receives and detects the wireless signal from transmitter 717, and in response thereto it commands release activator 709 to activate release 707. Although any form of wireless communication may be employed, typically optical or electromagnetic forms are employed. Note that due to the placement of sensor 715 it may be desirable to delay activation of release 707 for a period of time after generation of the signal by sensor 715. Such a delay may be incorporated in, or between, any of the elements along the path from and including sensor 715 to release 707. Although wireless signaling has been employed in the exemplary embodiment of the invention shown in FIG. 7, it is possible to employ wired forms of signaling in addition to such wireless forms, or in lieu thereof.

Adjustable stops 721 are employed to arrest the motion of moving block. Preferably, adjustable stops 721 should provide a dead impact, so that the motion of moving block 705 in the direction toward where product 701 had been initially suspended substantially immediately ceases.

Surface material 723 is a layer of material that corresponds to the surface against which the drop test is simulating the dropping of the product such as described hereinabove. Damage prevention material 769 is an optional layer of material to cushion the impact of product 701 against the top of the test apparatus. Those of ordinary skill in the art will recognize that embodiments of the invention may be arranged so that there is no top to the test apparatus within the area that product 701 is likely to move after impact with moving block 705, so that there is no need for damage prevention material 769.

In operation, product 701 is suspended at a desired impact angle above surface material 723 by suspension 703. Moving block 705 is then accelerated, as guided by guiding rods 711, to a desired impact velocity, which is selected using fundamental principles of mechanics to correspond to the desired dropping height. Note that a particular arrangement for accelerating moving block 705 is not shown, although any method, such as a) compressed air, b) hydraulic, c) springs, d) linear motors, e) rotary motors and a converter to linear motion, such as a pulley system, or f) the like may be employed. Advantageously, the impact velocity may be set to correspond to a drop which is greater than the distance between the closest point of product 701 and mainly block 705.

In accordance with an aspect of the invention, sensor 715 detects when the top of moving block 705, which is covered with surface material 723, just reaches the closest point of product 701 as it is suspended, and signals release activator 709, e.g., via wireless transmitter 717 and wireless control (WC) 719, to cause release 707 to release suspension 703. Advantageously, doing so permits product 701 to become a free body for the rest of the test. Substantially simultaneously with the release of suspension 703, surface material 723 impacts on product 701. The result of this impact will be forces upon product 701 which are substantially the same as those which would have been experienced by product 701 had it been dropped onto surface material 723 and impacted with the desired angle at the desired impact velocity. Furthermore, because product 701 has been released, it is now free to clatter and chatter in accordance with its natural dynamics and the properties of surface material 723.

Moving block 705 continues to move upward until it reaches and hits adjustable stops 721, at which point the motion of moving block 705 in the direction toward where product 701 had been initially suspended substantially immediately ceases. Preferably, moving block 705 will remain at the position in which its motion ceases. In order to achieve an accurate simulation of the result that would be achieved had product 701 been dropped from a height that would have resulted in it having the same velocity $V_0$ as moving block 705 had at the time of impact it is necessary that adjustable stops 721 be located a distance $h=V_0/\tau$ above the initial point of impact, where $\tau$ is the duration of clattering which results from the impact. Typically the value of $\tau$ is less than 50 ms.

Preferably, adjustable stops 721 should be positioned so that moving block 705 will cease moving toward product 721 at a point substantially one-half way up the height of the longest suspender, e.g., string, in suspension 703. In other words, the length of the longest suspender is 2 h. However, the length of the suspender above adjustable stops 721 is at the discretion of the implementor.

In another embodiment of the invention, suspension 703 could pass through holes in moving block 705, so that moving block 705 could be dropped, like a drop table, onto product 701. The downward motion of moving block 705 is arrested by adjustable stops 721, to prevent it from crushing product 701, and ultimately, the product lands on damage prevention material 769, which prevents the product from being destroyed.

The above described embodiments of the invention may be modified to use a low adhesive strength, i.e., weak, tape, either as the suspension or as the release. More specifically, in such an embodiment of the invention the first impact acts to perform the functions of the sensor and release mechanism by generating a force far greater than the tape, which effectively releases the product.

What is claimed is:

1. An apparatus for use in drop testing an object, comprising:
    means for suspending said object at a set angle;
    means for dropping said object and said suspending means so that there is substantially no relative motion between them; and
    means for effectively releasing said object from being suspended by said suspending means at a point in time prior to said object being subject to an impact as a result of being dropped;
    wherein said suspending means comprises a string.

2. The invention as defined in claim 1 wherein said means for dropping is a surface to which said means for suspending is attached.

3. The invention as defined in claim 1 wherein said means for dropping comprises a drop table.

4. The invention as defined in claim 1 wherein said means for dropping comprises a platform.

5. An apparatus for use in drop testing an object, comprising:
    means for suspending said object at a set angle;
    means for dropping said object and said suspending means so that there is substantially no relative motion between them; and
    means for effectively releasing said object from being suspended by said suspending means at a point in time prior to said object being subject to an impact as a result of being dropped;
    wherein said means for dropping comprises a drop table and wherein said object is subject to an impact with said drop table.

6. The invention as defined in claim 5 wherein said suspending means comprises a wire.

7. The invention as defined in claim 5 wherein said suspending means produces a very low restitutional force when deformed.

8. The invention as defined in claim 5 wherein said means for dropping comprises a drop table and wherein said means for suspending is coupled to said drop table.

9. The invention as defined in claim 5 wherein said means for effectively releasing comprises a mechanical sensor for determining when to disengage said suspending means from said object.

10. The invention as defined in claim 5 Wherein said means for effectively releasing comprises means for determining when to effectively release said suspending means.

11. The invention as defined in claim 5 wherein said suspending means is located at least in part above said dropping means.

12. The invention as defined in claim 5 further comprising a layer of material against which the drop test of said object is being performed.

13. An apparatus for use in drop testing an object, comprising:
    means for suspending said object at a set angle;
    means for dropping said object and said suspending means so that there is substantially no relative motion between them; and
    means for effectively releasing said object from being suspended by said suspending means at a point in time prior to said object being subject to an impact as a result of being dropped;
    wherein said means for effectively releasing comprises an electrical means for disengaging said suspending means for said object.

14. An apparatus for use in drop testing an object, comprising:
    means for suspending said object at a set angle;
    means for dropping said object and said suspending means so that there is substantially no relative motion between them; and
    means for effectively releasing said object from being suspended by said suspending means at a point in time prior to said object being subject to an impact as a result of being dropped;
    wherein said means for effectively releasing comprises an electrical sensor for determining when to disengage said suspending means from said object.

15. An apparatus for use in drop testing an object, comprising:
    means for suspending said object at a set angle;
    means for dropping said object and said suspending means so that there is substantially no relative motion between them; and
    means for effectively releasing said object from being suspended by said suspending means at a point in time prior to said object being subject to an impact as a result of being dropped;
    wherein said means for effectively releasing comprises an optical sensor for determining when to disengage said suspending means from said object.

16. Apparatus for performing drop testing for an object, comprising:
   a moveable surface;
   at least one tensile element that, when under tension, holds said object at a fixed angle with respect to said moveable surface while said moveable surface is moving; and
   a release that releases said tensile element from being under tension after said moveable surface is moving.

17. The invention as defined in 16 wherein said moveable surface is a surface of a drop table.

18. The invention as defined in 16 wherein said moveable surface is moveable toward said object.

19. The invention as defined in 16 wherein said moveable surface is a surface of a suspension platform.

20. The invention as defined in 16 wherein said tensile element comprises at least one of the set consisting of one or more: strings, wires, clamps, chain links, ball chain, or low adhesive strength tape.

21. The invention as defined in 16 wherein said release comprises at least one of the set consisting of one or more: a jaw, a gripper, a hook, a rocker arm, a magnetic clamp, a spool, a solenoid, a heatable glue, an explosive mechanism, a blade, a pair of scissors, or a low adhesive strength tape.

22. The invention as defined in 16 wherein said release is electronically activated.

23. The invention as defined in 16 further comprising an activator for said release.

24. The invention as defined in 16 further comprising at least one guiding red for guiding said moveable surface.

25. The invention as defined in 16 further comprising at least one sensor, and wherein said release is responsive to said at least one sensor to release said tensile element from being under tension after said surface is moving.

26. The invention as defined in 25 wherein said sensor comprises a sensor of at least one of a type of a set consisting of: electrical, mechanical, optical, chemical, and biological.

27. The invention as defined in 16 further comprising at least one pulse shaper.

28. The invention as defined in 16 further comprising a layer of material against which said drop test of said object is being performed.

29. An apparatus for use in drop testing an object, comprising:
   means for suspending said object at a set angle;
   means for dropping said object and said suspending means so that there is substantially no relative motion between them; and
   means for effectively releasing said object from being suspended by said suspending means at a point in time prior to said object being subject to an impact as a result of being dropped;
   wherein, any impulse resulting from said means for effectively releasing said object is substantially isolated from said object so that said impulse is not transmitted to said object.

30. A method for use in drop testing an object, comprising:
   suspending said object at a set angle;
   dropping said object while it is suspended, so that said object maintains said angle while it is falling; and
   effectively releasing said object from being suspended at a point in time after said objected is dropped but prior to said object being subject to an impact as a result of being dropped;
   wherein, any impulse resulting from said step of effectively releasing said object is substantially isolated from said object so that said impulse is not transmitted to said object.

31. An apparatus for use in drop testing an object, comprising:
   means for suspending said object at a set angle with respect to a surface against which said object will impact for said drop test at a set point of impact;
   means for causing relative motion between said object and said surface against which said object will impact for said drop test; and
   means for effectively releasing said object from being suspended by said suspending means at a point in time after development of said relative motion but prior to said object being subject to said impact with said surface;
   wherein said means for suspending substantially isolates said object from any impulse resulting from said means for effectively releasing said object releasing said object so that said impulse is not transmitted to said object.

32. An apparatus for use in drop testing an object, comprising:
   means for dropping said object so that it maintains a set angle with respect to a surface against which said object is to be dropped tested; and
   means for effectively releasing said object from being maintained at said angle at a point in time after said object is dropped and prior to said object being subject to an impact with said surface;
   wherein, any impulse resulting from said means for effectively releasing releasing said object is substantially isolated from said object so that said impulse is not transmitted to said object.

* * * * *